United States Patent [19]

Weed

[11] Patent Number: 5,370,605
[45] Date of Patent: Dec. 6, 1994

[54] CERVICAL VISUALIZATION HARNESS

[76] Inventor: Anna M. Weed, 15095 Lebanon Pinegrove Rd., Terry, Miss. 39170

[21] Appl. No.: 144,035

[22] Filed: Nov. 1, 1993

[51] Int. Cl.⁵ .......................... A61F 5/00; A61F 5/37
[52] U.S. Cl. ....................................... 602/35; 128/875
[58] Field of Search ................. 128/846, 869-876; 602/32, 34, 35, 36; 5/82 R

[56] References Cited

U.S. PATENT DOCUMENTS

| | | | |
|---|---|---|---|
| 2,252,357 | 8/1941 | Shaw | 128/874 |
| 2,751,594 | 6/1956 | Brissenden | 128/874 |
| 3,089,541 | 5/1963 | Lockshin . | |
| 3,136,311 | 6/1964 | Lewis | 128/874 |
| 3,137,294 | 6/1964 | Robertson | 128/874 |
| 3,204,256 | 9/1965 | Stollenwerk . | |
| 3,265,065 | 8/1966 | Jillson | 128/874 |
| 3,407,807 | 10/1968 | Giberson | 128/874 |
| 3,769,938 | 11/1973 | Hudziak | 128/874 |
| 3,889,668 | 6/1975 | Ochs | 128/870 |
| 4,010,744 | 3/1977 | Boyen | 602/32 |
| 4,383,524 | 5/1983 | Boger . | |
| 4,593,788 | 6/1986 | Miller . | |
| 4,627,428 | 12/1986 | Brooks | 128/873 |
| 4,672,958 | 6/1987 | Garman . | |
| 5,007,412 | 4/1991 | DeWall . | |
| 5,048,541 | 9/1991 | Haneline . | |
| 5,211,186 | 5/1993 | Shoemaker | 128/870 |

FOREIGN PATENT DOCUMENTS 74992 5/1989 Germany .
3124933 11/1986 Japan .

OTHER PUBLICATIONS

Publication "The Ultimate ™ Cervical Traction Strap for CT", No. P-590. MFD By AADCO, Inc., Randolph, V. T.

*Primary Examiner*—Michael A. Brown
*Attorney, Agent, or Firm*—Richard C. Litman

[57] ABSTRACT

A cervical visualization harness for use in applying traction to sedated and/or anesthetized patients. The cervical visualization harness includes a body portion and a pair of straps which extend from the body portion up over the shoulders of the patient and down the patient's body to appropriate points either between the patient's feet or to either side of the foot of the operating room table, to achieve a desired position of the patient's shoulders. The straps are secured to the OR table by hook and loop type fasteners. The hook and loop type fasteners allow for easy adjustment and removal of the straps. A string tie at the chest joins the two straps, keeping them centered relative to the patient. The patient's own weight holds the body portion of the cervical visualization harness intact. This cervical visualization harness and a method of using the same maximize patient care by increasing efficiency and minimizing incidental trauma which occurs during conventional treatment.

14 Claims, 4 Drawing Sheets

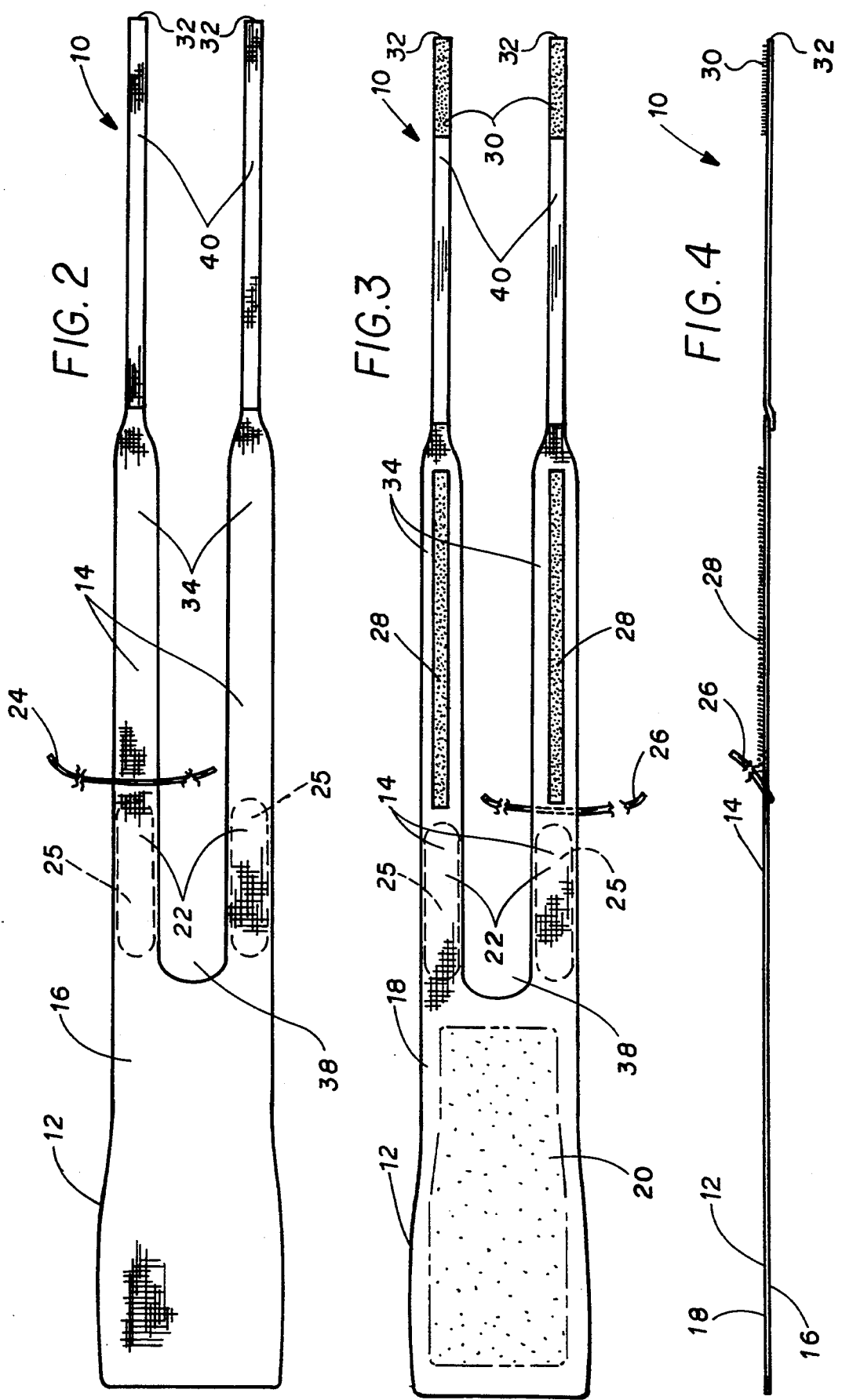

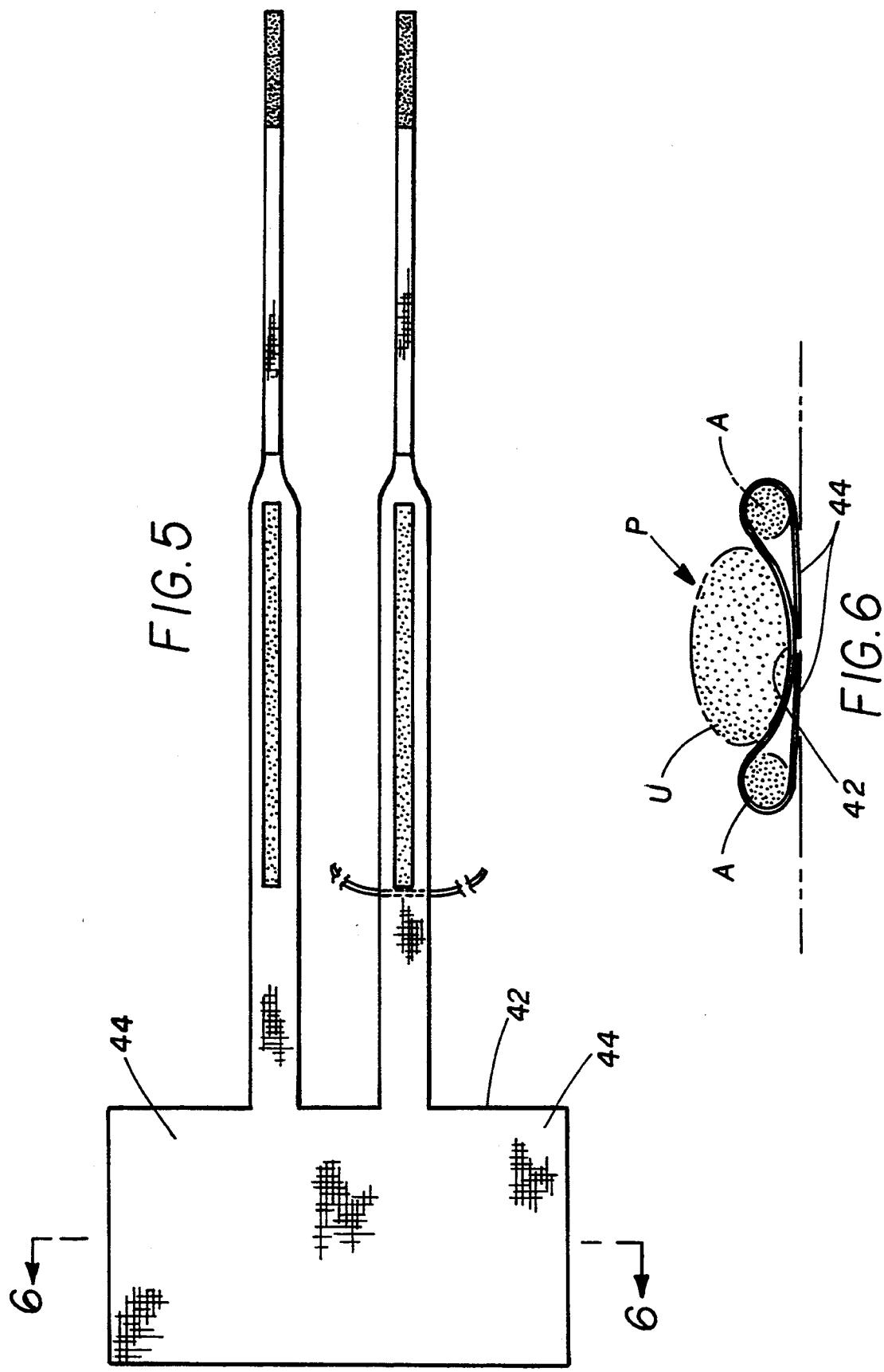

CERVICAL VISUALIZATION HARNESS

BACKGROUND OF THE INVENTION

1. Field of the Invention

The present invention relates to a shoulder traction device and, more particularly, to a surgically compatible shoulder traction device for use during an x-ray of a complete cervical spine.

2. Description of the Prior Art

Accurate documentation of surgical cases frequently dictates that x-rays be made. This invention addresses cervical procedures requiring cross-table lateral x-ray. Certain cervical x-ray procedures could benefit as well.

Presently, conventional methods for applying traction to the shoulders of a patient for proper visualization of the C6-7 interspace on x-ray dictate that the patient's shoulders be taped, such as with three inch adhesive. In accordance with this method or some variation thereof, an employee positioned under the sterile drapes pulls on the patient's wrists. The wrists are sometimes tied with strips of material, such as kerlix, to assist in pulling the arms and achieving the traction desired. This conventional method produces a reoccurrence of tape burns, occluded IVs, and employee back strains. Moreover, it jeopardized sterile fields and requires a repetition of incidental x-rays. The prolific recurrence of these disadvantages justifies the need for a corrective measure.

There exists a need for the development of a cervical visualization harness purposed to apply traction to the shoulders of a sedated and/or anesthetized patient in a supine position while minimizing trauma to the patient and healthcare professional as well as achieving maximum extension of the cervical spine during x-ray documentation. Harnesses for use in other areas are well known.

An example of such a harness is The Ultimate Cervical Traction Strap manufactured by AADCO, Incorporated of Vermont. This traction device eliminates broad shoulder artifact by applying traction directly to the shoulders and wrists of a patient. Two nylon webbing straps encircle the body from the shoulders to the feet of a patient and a torso strap supports the patient's arm comfortably against the body. Hook and loop type fasteners permit adjustment of the torso strap to virtually all size patients. Heavy-duty, quick release plastic buckles allow a healthcare professional to adjust easily the amount of traction tension being received by the patient. Unlike applicant's instant invention, the nylon webbing straps of the harness manufactured by AADCO, Incorporated cooperate with the patient's feet, and the torso strap encircles the upper torso of the patient. By contrast, applicant's instant invention is clearly of unitary construction including a pair of shoulder straps depending from a body portion. The body portion is placed under the patient's torso and the straps are drawn over each shoulder and down the patient's body to the end-slot or railing at the foot of the OR table or to either side of the foot of the OR table. In accordance with applicant's instant invention, key areas on the front of the patient's torso are exposed. Further, the straps cooperate with the OR table and do not rely on the patient's feet. Further yet, the straps are dimensioned and configured to reduce the amount of discomfort to the patient's shoulders.

In addition, harnesses have been the subject of patent protection in the prior art of record. One such harness is shown, for example, in U.S. Pat. No. 4,383,524, issued May 17, 1983 to Donald C. Boger. Boger discloses a traction aid for lowering the shoulder during lateral cervical spine radiographic procedures. The device employs a pair of wrist cuffs joined by a adjustable loop which extends around the underside of the feet of a patient in a supine position. Straightening the knees and extending the feet of the patient tensions the patient's arms and depresses the patient's shoulders. An alternative embodiment includes a pair of shoulder straps which encircle the shoulders of the patient and are joined to the leg straps to depress the shoulders by applying direct pressure. The mechanical interaction between the straps and the straightening of the patient's legs and feet produces the required depression. Similar to the above mentioned harness manufactured by ADDCO, Incorporated and unlike applicant's instant invention, the harness in the patent issued to Boger relies on a physical interaction with the patient to depress the patient's shoulders.

Other harnesses are shown and described in U.S. Pat. No. 3,137,294, issued Jun. 16, 1964 to Velma P. Robertson; U.S. Pat. No. 3,204,256, issued Sep. 7, 1965 to Hans Stollenwerk 5,048,541, issued Sep. 17, 1991 to Michael T. Haneline and in German Patent No. 74992, issued May 7, 1894 to P. Garstecki. The patent issued to Robertson teaches a body portion which covers the front torso of a patient as well as waist and shoulder straps depending therefrom. The shoulder straps extend over the shoulders of the patient and criss-cross behind the torso of the patient. The waist and shoulder straps cooperatively tie to a rail of the patient's bed to restrain the patient thereto. In the patent issued to Stollenwerk, a pair of straps are shown applied to a stretcher so as to criss-cross thereover to restrain the patient to the same. A strap is described in the patent issued to Haneline which restrains the midriff of a patient to a backboard of an x-ray station. Clearly, not one of these patents is shown to describe applicant's instant invention. The German patent shows a harness comprising a plurality of straps attachable to various areas of an OR table and which interact with a patient the maintain the patient in a supine position.

Although harnesses and the like are well known in the prior art, there are no surgically compatible harnesses for use during an x-ray of a complete cervical spine. Applicant proposes a cervical visualization harness suitable for surgical applications. Moreover, the instant invention disclosed hereinafter is of unitary construction and includes a non-skid surface to prevent the patient from slipping when used on slick surfaces, such as x-ray tables, padded shoulder straps to reduce patient discomfort, and string ties for securing the straps in a central position relative to the patient so as to be non-obstructing. None of the above inventions and patents, taken either singly or in combination, is seen to describe the instant invention as claimed.

SUMMARY OF THE INVENTION

The present invention relates to a surgically compatible shoulder traction device for x-ray of the complete cervical spine. The cervical visualization harness includes a body portion having a pair of straps extending therefrom. The cervical visualization harness is positionable on the operating room table over the sheet and under the draw sheet, with the non-skid surface facing downward and the straps folded and tucked under the head of the table. The positioning of the cervical visualization harness should insure that the origin of the straps be at the patient's axillae. An alternative embodiment includes a widened body portion which would eliminate the need for a draw sheet. The patient is positioned as desired on the OR table and prior to sterilization through the use of the straps. The body portion is placed under the patient's upper torso, and the straps are drawn over each shoulder and down the patient's body to either the end-slot or railing at the foot of the OR table disposed between the patient's feet, or most preferably to either side of the foot of the OR table. The straps are preferably criss-crossed and attached to the opposite and outer sides of the foot of the OR table so as to draw the patient's shoulders inward and downward. The straps are drawn through the end-slots or railings and are secured to themselves through hook and loop type fasteners. A tie located on one of the straps proximate the chest of the patient allows the pair of straps to be tied together, keeping the straps centrally disposed relative to the patient. The body portion of the cervical visualization harness may be wide enough so as to be permitted to be drawn over and around the patient's arms and tucked under the patient's upper torso such that the patient's arms are retained along side of the patient without the aid of a draw sheet. Once the patient's arms are tucked in either a draw sheet or the widened body portion of the cervical visualization harness, the sterilization procedure begins. If necessary, the hook and loop type fasteners enable the straps to be quickly released.

Accordingly, it is a principal object of the invention to provide a surgically compatible shoulder traction device for x-ray of the complete cervical spine.

It is another object that the device safeguard the integrity of the sterile field as well as avoid tape burns, not endanger IVs and EKG leads, and avoid inducement of employee back strains.

Another object is to add benefits accruing from the invention's nonconductive, washable construction, making it an indispensable piece of equipment.

It is a further object that the cervical visualization harness have an anti-skid backing for maintaining a desired orientation.

Still another object is that the cervical visualization harness have no metal parts and no irritating abrasive parts contacting the skin of the patient.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

FIG. 2 is a front elevational view of the cervical visualization harness shown in FIG. 1.

FIG. 3 is a rear elevational view of the cervical visualization harness.

FIG. 4 is a side elevational view of the cervical visualization harness.

FIG. 5 is a partial front elevational view of an alternative cervical visualization harness.

FIG. 6 a diagrammatic representational view of the alternative cervical visualization harness in use.

Similar reference characters denote corresponding features consistently throughout the attached drawings.

DETAILED DESCRIPTION OF THE PREFERRED EMBODIMENT

Figure 1A:
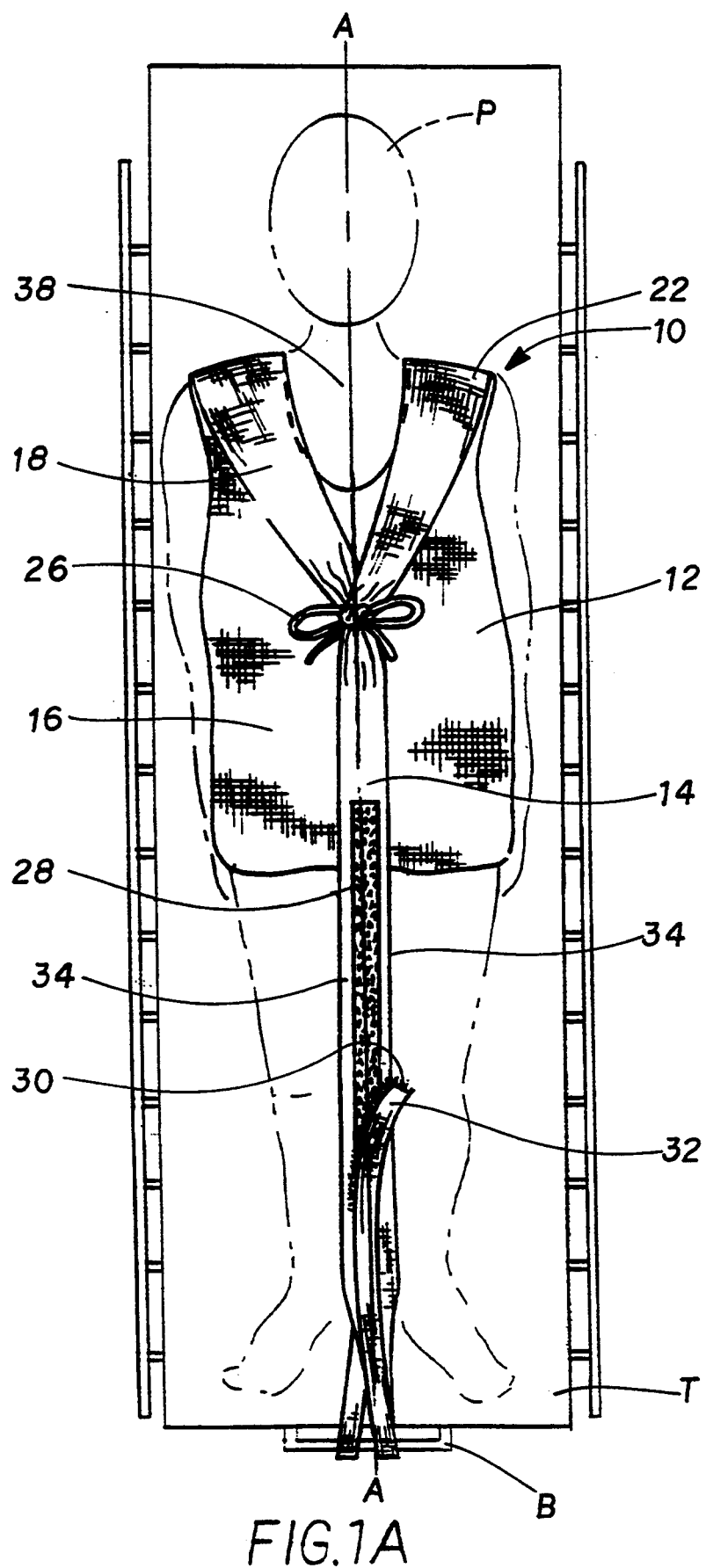
FIG. 1A is an environmental front elevational view of a cervical visualization harness according to the present invention fastened to the foot of an OR table.

The present invention, as shown in FIGS. 1 through 4, is a cervical visualization harness 10 (CV harness) for applying traction to the shoulders of a patient P during x-ray of the complete cervical spine. The CV harness 10 includes body portion 12 with a pair of straps 14 depending therefrom. The body portion 12 associates with the rear torso area of the patient P. The body portion 12 includes an inner surface 16 and an outer surface 18. The outer surface 18 has a non-skid surface area 20 to prevent the torso area of the patient P from sliding on a supporting surface. The non-skid backing 20 prevents sedated or anesthetized patients from slipping when being positioned on a slick surface, such as a x-ray table.

The straps 14 each originate from a respective upper corner of the body portion 12 forming shoulder regions 22 of the CV harness 10. The shoulder regions 22 may include built-in padding 25, as is shown in FIG. 6, to reduce discomfort to the patient's shoulders.

Figure 1B:
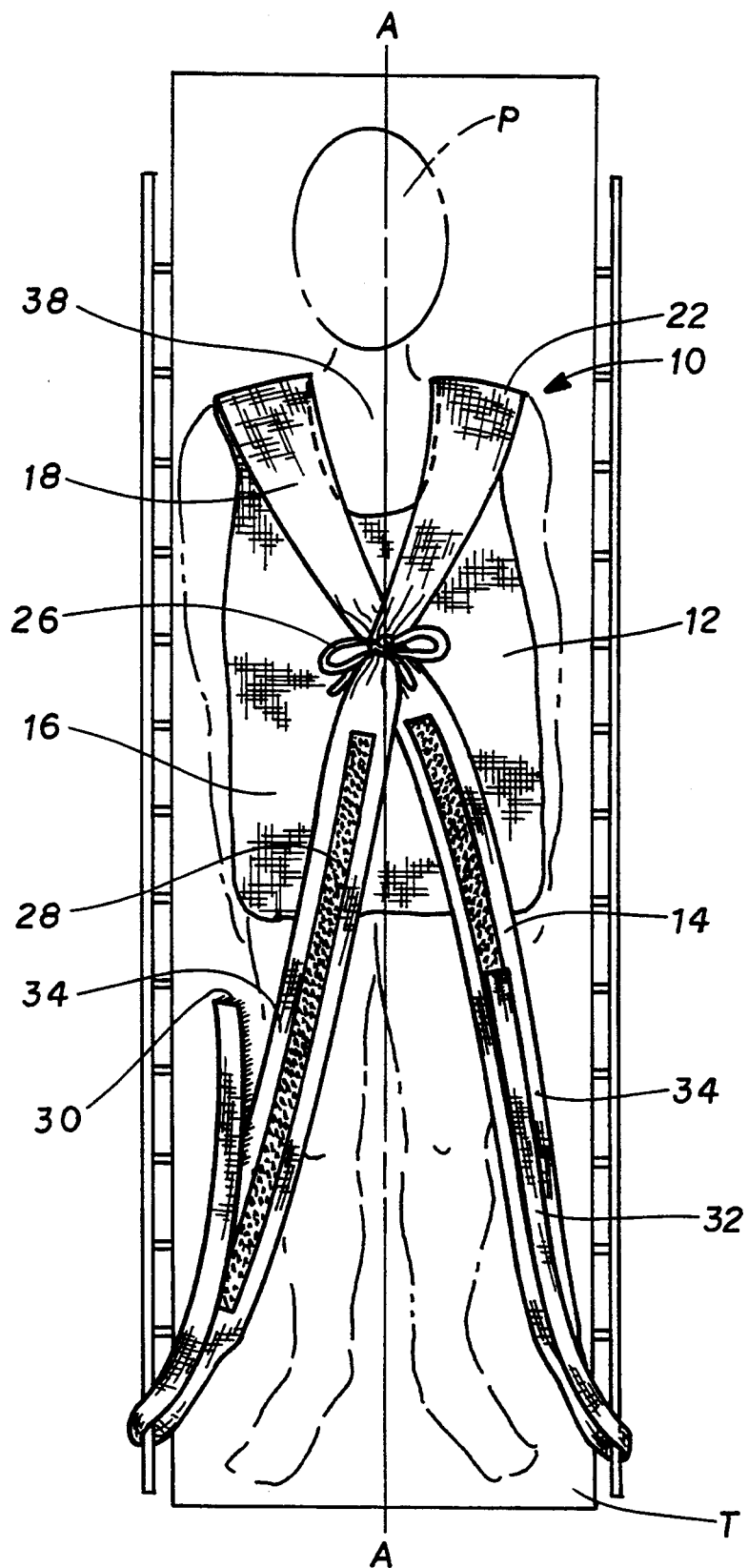
FIG. 1B is an environmental front elevational view of a cervical visualization harness fastened to the side railings of an OR table.

A string tie 26 is built-in to a certain one of the straps 14 a predetermined distance below the shoulder region 22. The string tie 26 functions in keeping the two straps 14 in close proximity to a midline of the CV harness defined by its longitudinal axis A—A, as is shown in FIG. 1. Keeping the two straps 14 along the midline A-A is especially advantageous when a bone graft retrieval is to be performed because the crest of the pelvis of the patient undergoing treatment will thereby remain exposed and unobstructed by the straps 14.

Each of the straps 14 includes a length of a soft loop portion 28 of a hook and loop type fastener. The loop portions 28 each originate a predetermined distance from the body portion 12 of the CV harness 10 and have a length sufficient to provide adequate adjustability of the CV harness 10.

Each of the straps 14 further includes a hard hook portion 30 of the hook and loop type fastener. Each hook portion 30 is disposed at a terminal end 32 of a respective strap 14 and is of sufficient length to adequately engage a respective matingly engageable loop portion 28.

With the exception of the string tie 26, each of the elements of the CV harness 10, that is, the non-skid backing 20, the loop portion 28, and the hook portion 30, are attached to one side, the outer surface 18, of the CV harness 10. This reduces the risk of irritation to the patient's skin.

Preferably, the length of the body portion 12 extends three feet (1 meter) and the length of each strap 14 extends ten feet (3 m), barring any adjustments needed to customize the harness for a particular table. This provides a CV harness 10 having an overall length extending thirteen feet (4 m). The body portion 12 is preferably two feet (70 centimeters) wide and may be wider, such as five feet (175 cm) wide, to secure the arms of the patient P alongside his or her torso.

The shoulder region 22 of each strap 14 is preferably six inches (15 cm) in width and two feet (70 cm) in length, rendering a neck opening 38 six inches (15 cm) wide. This region 22 may be padded to provide comfort to the patient. The straps 14 taper from the shoulder region 22 from a width of six inches (15 cm) to a width of two inches (5 cm) over a distance of four feet (120 cm) in length. Each loop portion 28 is of a length extending four feet (120 cm) and is attached to a tapering portion 34 of a respective strap 14, beginning adjacent a terminal end 32 of a respective shoulder region 22. The extent of each loop portion 28 provides adequate adjustability of the CV harness 10 for each individual patient. An intermediate portion 40 of the strap 14 extending between the loop portion 28 and the hook portion 30 is preferably three feet (1 m) in length. This is the preferred area for adjusting the desired length of each strap 14 in accordance with the table dimensions. A one foot (30 cm) length of the terminal end 32 of each strap 14 has attached thereto a respective hook portion 30 of corresponding length. The string tie 26 is preferably eighteen inches (45 cm) in length. It is found that a CV harness having these dimensions accommodates not only small patients but large and muscular patients as well.

The CV harness 10 is used to minimize trauma to a patient P, to protect the sterile field, to reduce possible employee back strain, and to minimized the repetition of x-rays due to an improper and insufficient traction on the shoulders. The CV harness 10 is placed on the OR table T in the operating room over the sheet (not shown) and under the draw sheet (also not shown) with the non-skid surface 20 down and the straps 14 tucked in under the cushion at the head of the table T. The draw sheet may be eliminated and the body portion 42, as is shown in FIG. 5, may be of sufficient width to permit each side 44 thereof to wrap up over the patient's arms A and back under the patient's torso U, as is shown in FIG. 6. If a rolled sheet or bolster (not shown) is to be placed under the cervico-thoracic spine, then it is placed under the CV harness 10. The patient P is placed on the OR table T on the CV harness 10 in the usual AP position. Once the patient P is positioned on the OR table T, normal preparation can begin without hindrance. After the patient P is sedated and/or anesthetized and prior to sterilization, the straps 14 are extended from over the patient's shoulders and through a slot in a bracket B attached to the foot of the OR table T between the patient's feet, or criss-crossed and attached to the sides of the foot of the OR table. Traction will then be applied until the proper position of each shoulder is acquired. A first portion, the hook portion 30, of the straps 14 will be secured to a second portion, the loop portion 28, of the strap 14 by way of the hook and loop type fastener, allowing the same to be easily adjusted and removed. The string tie 26 allows both of the straps 14 to be tied together, urging them off of the hip area of the patient P. Once the patient's arms are tucked in using the draw sheet of the OR table T. The CV harness 10 ensures that proper positioning of the patient P is maintained throughout the x-ray procedure and does not jeopardize the integrity of the sterile field.

During any cervical procedure performed, while the patient P is under sedation and/or anesthesia, x-rays are usually taken of localized regions. Discograms and anterior fusions are done with the patient P in a supine position. It is for this reason that discogram patients benefit from the CV harness 10 as well. Discogram patients remain awake and are normally unable to relax, causing difficulty in maintaining consistent positioning. However, proper instruction and application of the cervical visualization harness as well as emotional support directed to the patient P receiving treatment could ensure substantially problem free studies.

In use, the front of the patient's neck is exposed, as is the patient's hip area for bone graft retrieval, if desired. An IV is frequently located in the upper extremity of the patient P and EKG leads, either individual spot or back-pad type, are applied to the patient's upper body as well. With the use of the CV harness 10, the integrity of the sterile field remains safe; tape burns associated with applying traction in a conventional manner are avoided; IV's and EKG leads are not endangered; and employee back strains are avoided. Moreover, added benefits are provided by the nonconductive, washable construction, making this an indispensable piece of equipment.

In the event that a bracket B is not available on the OR table T, a table clip (not shown) is attachable to the foot of the OR table T for receiving the straps 14 therethrough. A bracket, such as a grabber bracket, No. 9-324, manufactured by AliMed of the Dedham, Mass., can be modified and used on certain OR tables other than those constructed of plexiglass material having a smooth edge and an approximate thickness of one-half inch (1 cm).

It is to be understood that the present invention is not limited to the sole embodiment described above, but encompasses any and all embodiments within the scope of the following claims.

I claim:

1. A harness for applying traction to the shoulders of a patient lying on a supporting surface, said harness consisting essentially of:
    a body portion having a non-skid outer surface;
    a pair of elongated straps depending from said body portion, said straps each having a terminal end and a medial portion, wherein said pair of elongated straps each depend transversely from said body portion and extends parallel to one another to form a substantially U-shaped configuration;
    a tie string fixed to one of said pair of elongated straps above said medial portion to hold said pair of elongated straps together at a midline of the patient; and
    means for fastening each one of said terminal ends to a respective one of said medial portions.

2. A harness according to claim 1, wherein said pair of elongated straps each depend from said body portion so as to form a neck opening therebetween.

3. A harness according to claim 1, wherein said body portion and said pair of elongated straps depending therefrom are each dimensioned and configured to be substantially planar and to have a nominal thickness.

4. A harness according to claim 1, wherein said body portion and said pair of elongated straps depending therefrom are each provided with padding.

5. A harness according to claim 1, wherein said body portion and said pair of elongated straps depending therefrom are each formed of a substantially pliable material.

6. A harness according to claim 1, wherein said pair of elongated straps each further include:
    a shoulder region depending from said body portion;
    a tapered portion extending from said shoulder region; and
    a generally narrow portion having a substantially constant width extending from said tapered portion,
    said generally narrow portion and said tapered portion forming said medial portions.

7. A harness according to claim 6, wherein said shoulder region is provided with padding.

8. A harness according to claim 6, further including means for successively joining said tapered portion, said intermediate portion, and said terminal end in series with one another, and wherein
said body portion is integral with each one of said shoulder regions which are, in turn, integral with a respective one of said tapered portions.

9. A harness according to claim 1, wherein said fastening means includes a hook and loop type fastener having a first element and a second element being matingly engageable with said first element, wherein
said medial portion of each one of said pair of elongated straps has said first element of said hook and loop type fastener attached thereto, and wherein
said terminal end of each one of said pair of elongated straps has a second element of said hook and loop type fastener attached thereto, each one of said terminal ends being foldable back adjacent to and matingly engageable with a respective one of said medial portions.

10. A harness according to claim 9, wherein said first element includes a soft loop portion of said hook and loop type fastener and said second element includes a hook portion of said hook and loop type fastener.

11. A harness for applying traction to the shoulders of a patient lying on a supporting surface, said harness consisting essentially of:
body portion having an inner surface and an outer surface, said outer surface being a non-skid surface;
a pair of elongated straps depending from said body portion, said straps having:
an inner surface and including a shoulder region,
a first elongated region having an elongated strip of loop portion attached to said inner surface thereof,
second elongated region having a hook portion attached to an inner surface thereof, and
a third elongated region intermediate said first elongated region and said second elongated region, said loop portion being matingly engagable with said hook portion to form a hook and loop fastening arrangement; and
a tie string fixed to a first one of said pair of elongated straps for tying said first one of said pair of elongated straps to a second one of said pair of elongated straps to hold said pair of elongated straps along a midline of the patient;
wherein said pair of elongated straps each depend transversely from said body portion and extends parallel to one another to form a substantially U-shaped configuration.

12. A harness according to claim 11, wherein said pair of elongated straps each depend transversely from said body portion and extend parallel to one another so as to form a substantially U-shaped configuration.

13. A harness according to claim 11, wherein said body portion and said pair of elongated straps depending therefrom are each dimensioned and configured to be substantially planar and to have a predetermined thickness.

14. A harness according to claim 11, wherein said body portion and said pair of elongated straps depending therefrom are each formed of a substantially pliable material.

* * * * *